(12) United States Patent
Colleran et al.

(10) Patent No.: US 12,733,923 B2
(45) Date of Patent: Sep. 15, 2026

(54) CANNULA WITH SUTURE LOCK

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Dennis P. Colleran, North Attleboro, MA (US); Nehal N. Patel, Boston, MA (US); Timothy Young, Upton, MA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 68 days.

(21) Appl. No.: 18/777,872

(22) Filed: Jul. 19, 2024

(65) Prior Publication Data

US 2025/0025154 A1 Jan. 23, 2025

Related U.S. Application Data

(60) Provisional application No. 63/528,008, filed on Jul. 20, 2023.

(51) Int. Cl.
*A61B 17/06* (2006.01)

(52) U.S. Cl.
CPC .................. *A61B 17/06004* (2013.01); *A61B 2017/06009* (2013.01); *A61B 2017/06019* (2013.01); *A61B 2017/06052* (2013.01)

(58) Field of Classification Search
CPC ........... A61B 17/0482; A61B 17/0483; A61B 17/06004; A61B 2017/0496; A61B 2017/06009; A61B 2017/06019; A61B 2017/06052; A61B 2090/036
See application file for complete search history.

(56) References Cited

U.S. PATENT DOCUMENTS

2016/0310125 A1* 10/2016 Spivey .................. A61B 17/17

* cited by examiner

*Primary Examiner* — Mohamed G Gabr
(74) *Attorney, Agent, or Firm* — ArentFox Schiff LLP; Joseph M. Maraia

(57) ABSTRACT

A cannula includes an elongated body having a proximal end, a distal end, and a longitudinal axis extending therebetween, a first surface configured for passage of a surgical instrument along the first surface, and a second surface opposite the first surface. A passageway extends along the second surface, which is configured for passage of a suture. An eyelet is at least partially defined through the second surface at the distal end of the body for receiving the suture at the distal end.

17 Claims, 14 Drawing Sheets

1000
102a
94b
102
98
102b 1000
102a
94b
94a
16
102
96b
102b 1210
1200
112

1206a
1204
1202
1200
16
18
1206
1206b 1206a
1206
18
16
1202
1200
16
1206b

CANNULA WITH SUTURE LOCK

CROSS REFERENCE TO RELATED APPLICATIONS

This application claims benefit under 35 U.S.C. § 119 to U.S. Provisional Application No. 63/528,008, filed on Jul. 20, 2023, entitled CANNULA WITH SUTURE LOCK, the entire contents of which are incorporated herein by reference for all purposes.

FIELD

The present disclosure relates to a cannula, and, more particularly, to systems and methods for passing instruments and traction sutures by way of a cannula.

BACKGROUND

Hip arthroscopy, also known as hip arthroscopic surgery, is a minimally invasive surgical procedure used to diagnose and treat certain conditions affecting the hip joint. It often involves the use of a specialized instrument called an arthroscope, which is a thin, flexible tube with a camera and light source attached to it. The arthroscope can be inserted into small incisions around the hip joint, allowing the surgeon to visualize and access the internal structures of the joint.

During hip arthroscopy, the surgeon typically creates small incisions around the hip joint to insert the arthroscope and other surgical instruments. The hip capsule can then be accessed and often partially or completely released or cut to allow better visualization and access to the internal structures of the joint. By releasing or cutting the hip capsule, the surgeon gains increased mobility and maneuverability within the joint, facilitating the examination and treatment of various conditions. This includes addressing labral tears, femoroacetabular impingement (FAI), loose bodies, synovial conditions, and other abnormalities that may be causing pain or limiting hip joint function. However, at times, the hip capsule can interfere with a surgeon's ability to view anatomy during surgical tasks.

SUMMARY

The proposed approach includes a cannula system that combines a cannula with a capsule stitch. Embodiments of the proposed approach vary in the way the suture cooperates with the cannula. Once the incision through the hip capsule is completed, the capsule suture can be placed through the capsule tissue. One may place the capsule stitch in a location that supports traction on the capsule to improve visualization. The suture can then be threaded through the cannula suture eyelets/canals to control/manage the suture and keep the suture from interfering with instruments, implants and/or other sutures used in the procedure. Further, the suture can be tied, cleated or wedged to secure the desired tension.

Further examples of the cannula system of this disclosure may include one or more of the following, in any suitable combination.

In examples, the system includes a cannula, including an elongated body having a proximal end, a distal end, and a longitudinal axis extending therebetween, a first surface configured for passage of a surgical instrument along the first surface, and a second surface opposite the first surface. A passageway extends along the second surface, which is configured for passage of a suture. An eyelet is at least partially defined through the second surface at the distal end of the body for receiving the suture at the distal end.

The system may further include a proximal securing component defined at the proximal end of the elongated body. In some examples, the proximal securing component includes one or more securing members against the second surface for securing limbs of the suture passed through the passageway and received at the distal end. the proximal securing component is configured to secure the limbs of the suture to the elongated body via a knot and/or a cleat. The one or more securing members may include two or more wings configured to secure the limbs of the suture to the elongated body via the knot and/or the cleat.

In some examples of the system, the proximal securing component may be configured to secure the limbs of the suture to the elongated body via a locking component. In some examples, the locking component includes a foot. In some examples, the locking component is slidably configured along the securing member to further secure the suture.

In some examples of the system, the system may further include one or more suture tunnels disposed along the first surface, the one or more suture tunnels configured for passage of limbs of the suture therethrough. The locking component may be configured to allow the suture to be adjusted during usage without unsecuring the suture from the securing member. In some examples of the system, the second surface is configured to receive one or more hemostats. In some examples, the one or more hemostats compress the suture and the second surface at an insertion site to create elevation of a tissue, wherein the one or more hemostats are further configured to maintain contact with a patient at an insertion site to further secure the limbs of the suture during use of the cannula.

In some examples of the system, a location of the suture at the eyelet is selected to prevent interference with the surgical instrument and/or a surgical implant. In some examples, the location of the suture at the eyelet is more distal to facilitate insertion of the cannula through the insertion site to the tissue. In some examples of the system, the proximal end of the elongated body comprises a textured gripping surface. In some examples, the one or more suture tunnels includes a grooved chamber.

The proposed approach also includes a method for implementing a surgical procedure. The method includes, in part, making an incision on a patient in need of such surgical procedure at a location proximate an operation site to establish an entry portal at an external surgical site. The method also includes passing a suture through the surgical site to reach an internal surgical site. The method may further include measuring the portal depth from the external surgical site to the internal surgical site. The method may also include threading the suture through a cannula to form a cannula system with or without the use of a monofilament to thread a suture through the cannula system. The cannula system includes an elongated body having a proximal end, a distal end, and a longitudinal axis extending therebetween, a first surface configured for passage of a surgical instrument along the first surface, and a second surface opposite the first surface. The cannula system also includes a passageway extending along the second surface, the passageway configured for passage of the suture. The cannula system includes an elongated body having a proximal end, a distal end, and a longitudinal axis extending therebetween, a first surface configured for passage of a surgical instrument along the first surface, and a second surface opposite the first surface. The cannula system also includes a passageway extending along the second surface, the passage way configured for passage of the suture. The cannula system may further include an eyelet at least partially defined through the second surface at the distal end of the body for passage of the suture through the distal end of the elongated body. The cannula system also includes a proximal securing component on the second surface for securing limbs of the suture passed through the passageway and passed around the distal end. The method may further include, inserting the cannula system through the external surgical site, cleating the suture to the elongated body, and adjusting the suture against the patient.

In examples of the method, the second surface is configured to receive one or more hemostats. One or more hemostats compress the suture and the second surface at an insertion site to create elevation of the tissue, and the one or more hemostats are further configured to maintain contact with a patient at an insertion site to further secure the limbs of the suture during use of the cannula.

In examples of the method, the proximal securing component is configured to secure the limbs of the suture to the elongated body via a locking component. The locking component is slidably configured along the second surface to further secure the suture, and the locking component is configured to allow the suture to be adjusted during usage without unsecuring the suture from the securing member.

A reading of the following detailed description and a review of the associated drawings will make apparent the advantages of these and other features. Both the foregoing general description and the following detailed description serve as an explanation only and do not restrict aspects of the disclosure as claimed.

BRIEF DESCRIPTION OF THE DRAWINGS

Reference to the detailed description, combined with the following figures, will make the disclosure more fully understood, wherein.

DETAILED DESCRIPTION OF THE INVENTION

Figure 1A:
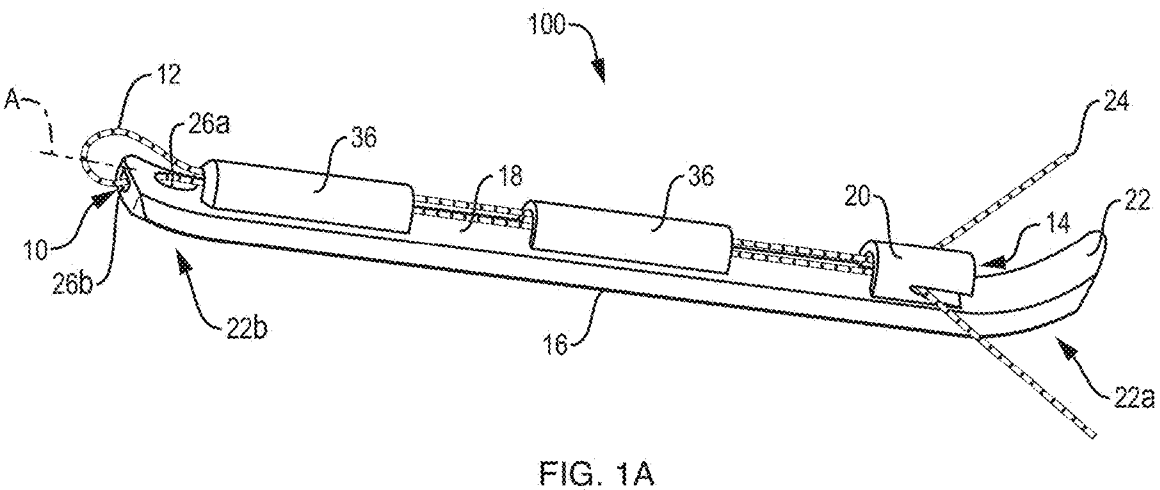
FIG. 1A illustrates an example of a cannula system, in a perspective view.

In the following description, like components have the same reference numerals, regardless of different illustrated examples. To illustrate examples clearly and concisely, the drawings may not necessarily reflect appropriate scale and may have certain features shown in somewhat schematic form. The disclosure may describe and/or illustrate features in one example, and in the same way or in a similar way in one or more other examples, and/or combined with or instead of the features of the other examples.

In the specification and claims, for the purposes of describing and defining the invention, the terms "about" and "substantially" represent the inherent degree of uncertainty attributed to any quantitative comparison, value, measurement, or other representation. The terms "about" and "substantially" moreover represent the degree by which a quantitative representation may vary from a stated reference without resulting in a change in the basic function of the subject matter at issue. Open-ended terms, such as "comprise," "include," and/or plural forms of each, include the listed parts and can include additional parts not listed, while terms such as "and/or" include one or more of the listed parts and combinations of the listed parts.

FIG. 1A illustrates an example of a perspective view of cannula system 100 providing a passageway combining cannula with suture in accordance with this disclosure. In examples, this system 100 may generally comprise a substantially cylindrical, elongated body 22 having a proximal end 22*a* and a distal end 22*b* along a longitudinal axis extending therebetween. Although the elongated body 22, along with others in this disclosure, may resemble a half cylinder, in some implementations, a full cylindrical elongated body is also possible. In examples, elongated body 22 may angle away from the longitudinal axis at one or both of the proximal end 22*a* and the distal end 22*b* to more readily provide an area for a user to manipulate and secure cannula system 100 during use. For example, a user can better grasp proximal end 22*a* during a surgical procedure, which can be seen in FIG. 4D. Cannula system 100 may include a first surface 16 configured for passage of a surgical instrument along first surface 16. Examples of surgical instruments can include, but are not limited to: shavers, burrs, implants, suture management tools, general arthroscopic instruments, trocars, arthroscopic graspers, arthroscopic scissors, arthroscopic dissectors, arthroscopic needle holders, arthroscopic suturing devices, grasping forceps, hook retractors, electrosurgical devices, suction-irrigation systems, and/or sutures. As shown in FIG. 1A, first surface 16 can comprise the underside of cannula system 100, providing access for the passage of surgical instruments and/or implants into a surgical site. Examples of surgical instruments can include, but are not limited to: labral anchors, suture anchors, osteochondral plugs, microfracture awls, hip prostheses, bone screws, bone cement. Cannula system 100 may further include a second surface 18 opposite of first surface 16. Also shown in FIG. 1A, second surface 18 can comprise the topside of cannula system 100. One or more passageways 14, which can also be referred to as portals and/or channels, can extend along second surface 18, and in some examples, can be configured to contain and facilitate the passage a suture and/or stitch, such as suture 24, while remaining separate from the passage of instruments along the concavity of first surface 16. Alternatively, the second surface 18 may include holes which the suture 24 is fed through and tied off around to secure the suture 24. In examples, suture 24 can be a traction suture/stitch. Suture 24 can be referred to both holistically, and by its limbs, for example.

Also shown in FIG. 1A, one or more securing members 20, which can also be referred to as a proximal securing component, can be disposed on, or in some examples, secured to, components of, the second surface 18 to form passageway 14, secure limbs of the suture 24 as it passes through the passageway 14, and loops around patient tissue at the distal end 22*b* of elongated body 22. To enable this looping around at loop 12, cannula system 100 can further include a through hole or eyelet, such as eyelet 10, at the distal end 22*b* of elongated body 22. While eyelet 10 along with others in this disclosure, may include only a single eyelet in some implementations, additional eyelets are also possible to further provide suture management. In examples, through eyelet 10 includes a first opening 26*a*, which can be an oval-shaped eyelet/divot, in second surface 18 at distal end 22*b* and a second opening 26*b* at the tip of distal end 22*b*. In this way, a first limb of the traction suture 24 passes through tissue at loop 12 during use at a site, such as at patient's hip capsule. To summarize, through eyelet 10 can enclose suture 24 as it is threaded from proximal end 22*a* of elongated body 22 by way of passageway 14 within one or more suture tunnels 36, before being threaded at loop 12 at distal end 22*b* around patient tissue before a second limb of traction suture 24 reenters passageway 14 and is threaded back toward proximal end 22*a* of elongated body 22. The suture 24 can then be tied, cleated, wedged, or otherwise secured to provide the desired force/tension throughout cannula system 100. As an illustrative example, during surgery, once an incision through a hip capsule is completed, suture 24, prior to being secured within cannula system 100, can be placed through the capsule tissue to retract soft-tissue from a surgical location to allow for better viewing during the surgical procedure. The suture 24 can then be threaded through the passageway 14 by way of one or more suture tunnels 36 of cannula system 100 to control/manage the suture 24 and keep the suture 24 from interfering with instruments, implants and/or other sutures that may be used in a surgical procedure, before suture 24 can subsequently be secured (for example, via a knot, foot, and/or locking component) by proximal securing component 20 and/or at the site of insertion into a surgical site, such as site 120. This can be seen in FIGS. 3-4E, and will be discussed further throughout the disclosure.

Figure 1B:
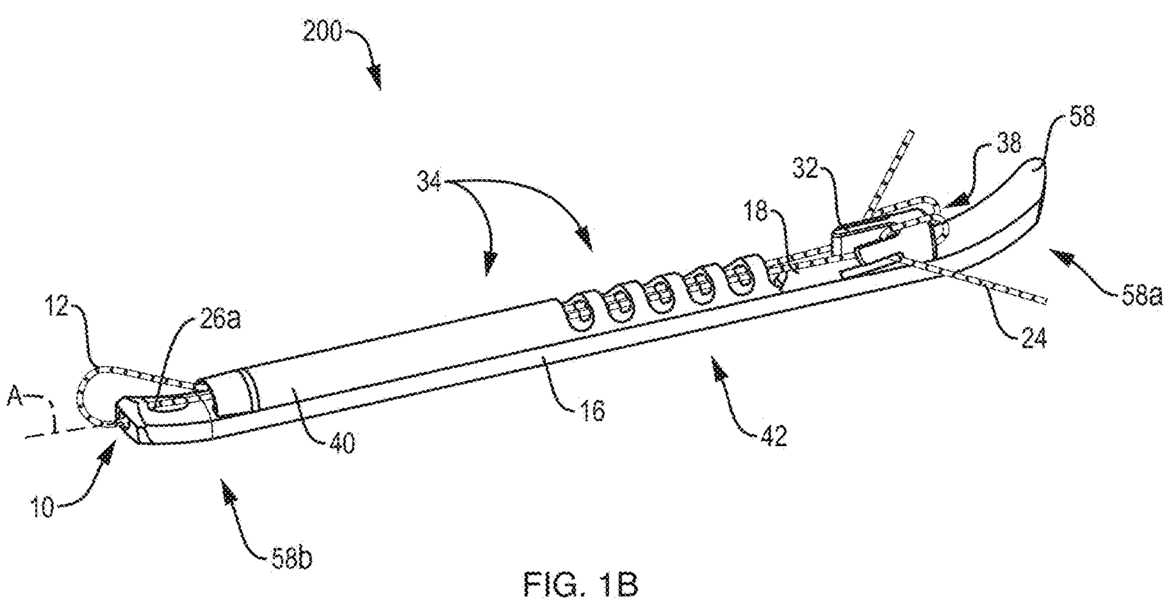
FIG. 1B illustrates an example of an additional cannula system, in a perspective view.

FIG. 1B illustrates an example of a perspective view of cannula system 200 providing a passageway/portal 38 for both cannula and suture in accordance with this disclosure. Alternate implementations of the proposed approach may vary in the way the suture cooperates with the cannula within a cannula system. For example, cannula system 200 is substantially similar to cannula system 100. However, there may be some structural differences. In FIG. 1B, similarly to cannula system 100, suture 24 can be threaded through the one or more suture tunnels 34 of cannula system 100 to control/manage the suture 24 and keep the suture 24 from interfering with instruments, implants and/or other sutures that may be used in a surgical procedure. However, suture 24 can then be tied, fastened, or otherwise secured to proximal securing component 32 at proximal end 58*a* of elongated body 58. This orientation of cannula system 200 can allow the surgeon to pull/adjust the suture 24 during usage without unsecuring, untying, and/or uncleating the suture 24, which may not be possible in cannula system 100. In some implementations, this will increase displacement of the hip capsule temporarily to gain better temporary visualization for a certain task within the surgery. For example, the cannula system 200 can allow the surgeon to use existing channels/passageway/portal, such as portal 38, to create traction on the hip capsule to improve visualization. As a result, the surgeon may not have to create additional incisions to add traction. The cannula system's 200 eyelets/channels 38 can thereby manage the traction suture 24 and keep it from interfering with, for example, instruments and implants that may pass through the portal 38 to the surgical site. In some implementations, the use of quick suture locking features (i.e. cleats) can allow the surgeon to quickly lock, unlock, adjust the tension of suture 24 as needed throughout the procedure.

Figure 1C:
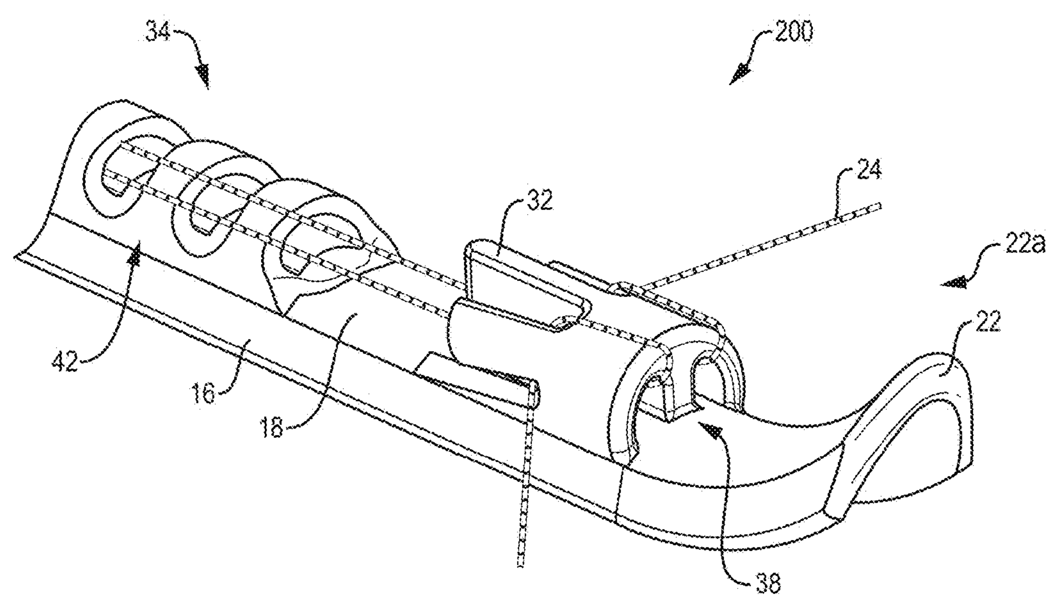
FIG. 1C illustrates an example of the cannula system of FIG. 1B, in a zoomed-in perspective view.

FIG. 1C illustrates an additional view of cannula system 200. As shown in FIGS. 1B and 1C, in some examples, suture 24 is visibly secured to proximal securing component 32 of cannula system 200. Additionally, and differing from cannula system 100 of FIG. 1A, one or more suture tunnels 34 providing a passageway/portal 38 for suture 24 may be individually distinct in form and/or function. For example, while suture tunnel 40 of one or more suture tunnels 34 operates primarily to enclose and stabilize suture 24 within cannula system 200, much like one or more suture tunnels 20 of cannula system 100, suture tunnels 42 can also provide additional security to suture 24 during usage. This can be seen in another implementation in FIG. 2D, where an external locking component is introduced to compress and initially (as shown in FIG. 2D) and/or further secure (as shown in FIGS. 1B and 1C) suture 24 during usage. FIG. 1C demonstrates the suture 24 threaded through cannula suture tunnels 34 and then tensioned and locked by use of cleat. In some implementations, the cleat works in the direction of pulling tension, so that any temporary additional tensioning of the suture 24 can further lock the suture 24 and not "uncleat" the suture during surgery. Additionally, the bifurcated "nostril" design of proximal securing component 32 of cannula system 200 can also allow the surgeon to tie the two suture limbs of suture 24 against the respective "nostrils" of the proximal securing component 32, giving the surgeon a second securement option.

Figure 2A:
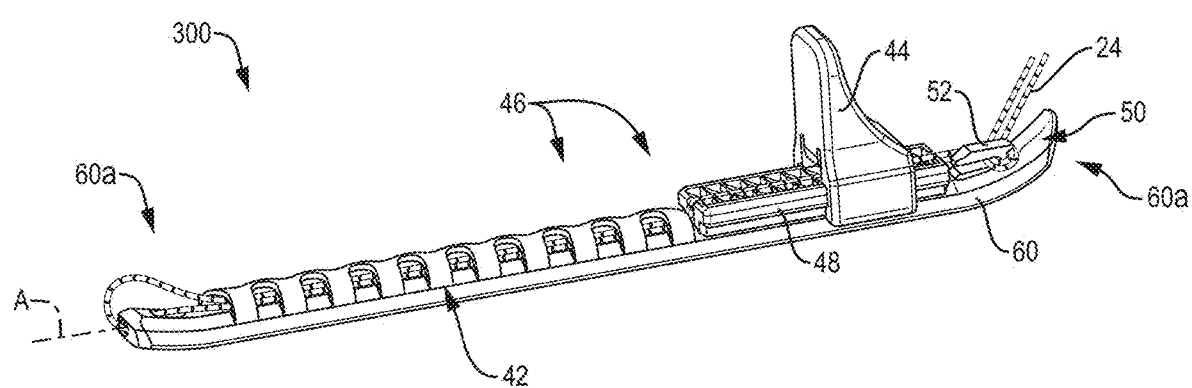
FIG. 2A illustrates an example of a third cannula system, in a perspective view.
Figures 2B, 2C, 2D:
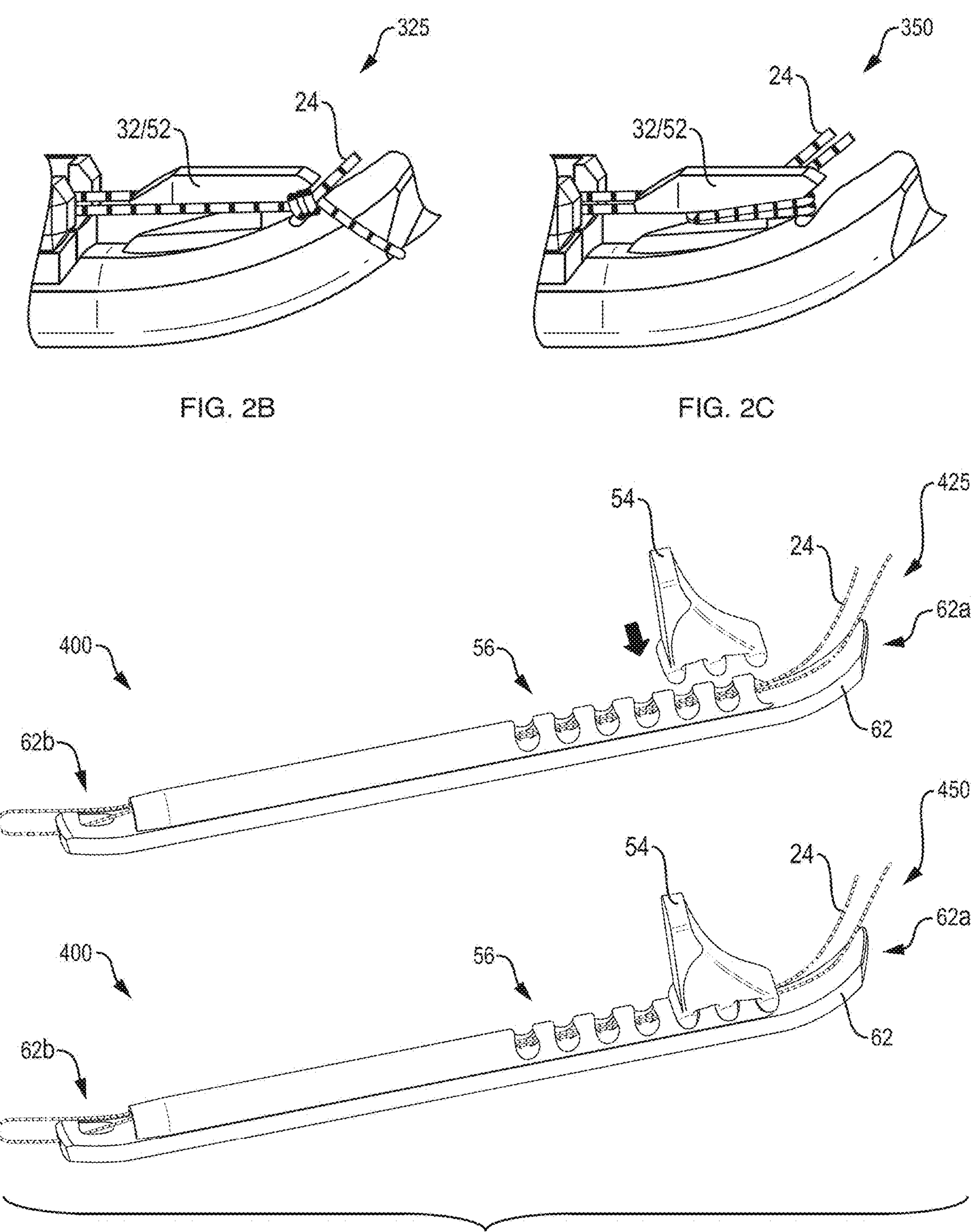
FIG. 2B illustrates an example of a suture secured via a tie knot to a cannula system, in a zoomed-in perspective view.
FIG. 2C illustrates an example of a suture secured via a cleat knot to a cannula system, in a zoomed-in perspective view.
FIG. 2D illustrates an example of a fourth cannula system, in before and after perspective views.

FIG. 2A illustrates an example of an additional cannula system 300 providing a single passageway/portal 50 and including locking component 44. As with cannula systems 100 and 200, alternate implementations of the proposed approach may vary in the way the suture cooperates with the cannula within a cannula system. For example, cannula system 300 is substantially similar to cannula systems 100 and 200. However, there may also be some structural differences. In this example, locking component 44 is slidably configured to further secure suture 24 during use of cannula system 300, similar to the external locking component shown in FIG. 2D. In some examples, such as in FIG. 2A, locking component 44 is an internal component within cannula system 300, rather than an external component which can be separately introduced as needed, as in FIG. 2D. The present example of cannula system 300 also includes one or more suture tunnels 46, which can include suture tunnels 42, which may operate similarly to suture tunnels 42 of cannula system 200 to provide additional security to suture 24 during usage by permitting the introduction of an additional external locking component, as shown in FIG. 2D. However, as shown in FIG. 2A, one or more suture tunnels 46 also can include grooved chamber 48 to facilitate the sliding and securing functionality of locking component 44 within cannula system 300 at proximal end 60*a* of elongated body 60. In this way, suture 24 can be readily adjusted and re-secured for tautness and/or slack with additional adjustability, even as suture 24 may be tied, fastened, or otherwise secured to proximal securing component 52 for a baseline level of suture security, similar to the dynamic provided by proximal securing component 32 of cannula system 200 in FIGS. 1B and 1C.

FIGS. 2B and 2C illustrate examples of suture 24 when secured to a proximal securing component of a cannula system, such as proximal securing components 32 and/or 52 of cannula systems 200 and 300, respectively. In this way, view 325 of FIG. 2B shows suture 24 secured to a proximal securing component of an elongated body of a cannula system via a tic knot. This is similar to how suture 24 is secured in cannula systems 100 and 200, as shown in FIGS. 1A-1C. View 350 of FIG. 2C shows suture 24 secured to a proximal securing component of an elongated body of a cannula system via a cleat knot. This is similar to how suture 24 is secured in cannula system 300, as shown in FIG. 2A.

FIG. 2D illustrates an example of an additional cannula system 400 providing a single portal when engaged with a locking component 54, in before and after perspective views 425 and 450, respectively. As with previous cannula systems, alternate implementations of the proposed approach may vary in the way the suture cooperates with the cannula within a cannula system. For example, cannula system 400 is substantially similar to cannula systems 100, 200, and 300. However, there may also be some structural differences. In this example, locking component 54, which can also be referred to as a foot, is an external locking component, which can be separately introduced as needed. As mentioned previously, this process of introduction is detailed in before and after perspective views 425 and 450, respectively, as external locking component 54 is introduced and secured into the grooves of suture tunnels 56 at proximal end 62*a* of elongated body 62. Suture tunnels 56 can be similar to suture tunnels 42 within cannula system 300, as previously introduced in FIG. 2A.

Figure 2E:
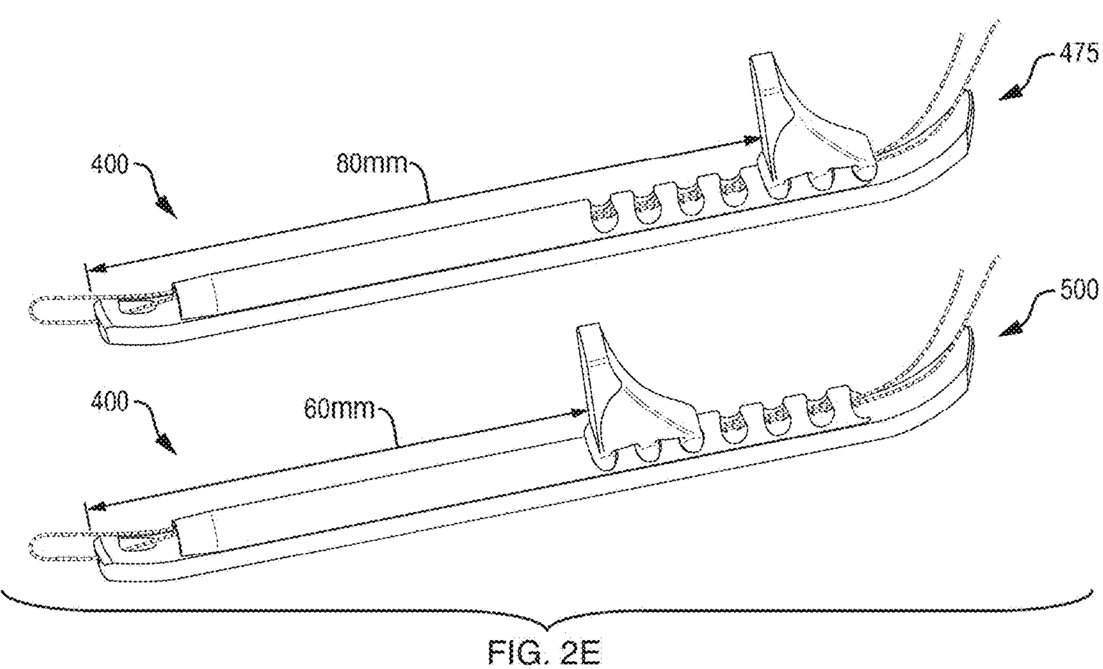
FIG. 2E illustrates examples of the cannula system of FIG. 2D when engaged with a locking component at different suture depths, in a perspective view.

FIG. 2E illustrates example views 475 and 500 of cannula system 400 of FIG. 2D when engaged with the locking component 54 at different suture depths of 80 and 60 mm, respectively. As shown in FIGS. 2D and 2E, and unlike in cannula systems 100, 200, and 300, no proximal securing component or additional securing mechanism is present in cannula system 400, by which suture 24 may be secured. In this way, locking component 54 can be inserted and secured at different depths along suture tunnels 56 to allow for suture 24 to be readily adjusted and re-secured for tautness and/or slack as the means of primary/sole length adjustability. This can allow for more dynamic adjustability of suture 24 length during usage by not requiring initial tying, knotting, or other baseline securing to the cannula system. Additionally, in some implementations, locking component 54 can also be used as a foot to provide contact against the skin to better hold suture 24 tension. For example, in FIG. 2E, adjusting locking component 54 to the portal depth from skin to the capsule anatomy can be achieved by moving locking component 54 from an 80 mm depth to 60 mm, as shown in view 475 and 500, respectively. The locking component 54 can thereby help retain suture 24 tension throughout surgery, while still allowing for the temporary increase in tension by pulling the traction suture 24 ends and cannula system 400 for certain surgical tasks.

Figure 2F:
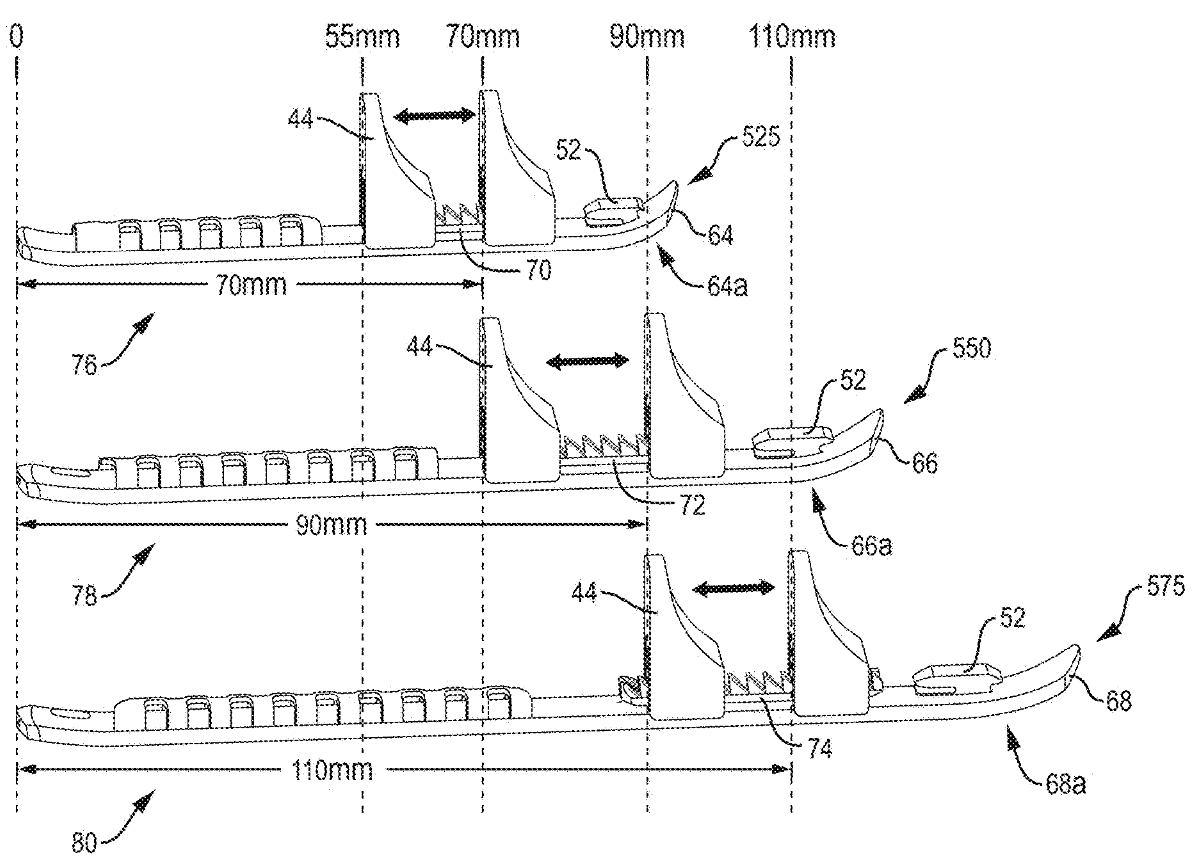
FIG. 2F illustrates examples of a cannula system similar to that shown in FIG. 2A when engaged with a locking component at different suture depths, in a perspective view.

FIG. 2F illustrates example cannula systems 525, 550, and 575, which may be similar to example cannula system 300 of FIG. 2A. In FIG. 2F, locking component 44 is shown to be slidably configured to further secure suture 24 (not shown) during use of cannula systems 525, 550, and 575 at their respective and individually varying example cover, grooved chamber, and elongated body portal depths/lengths in order to cover a wide range of patient anatomies. In some implementations, respective example suture tunnels, grooved chambers, and elongated bodies of cannula systems 525, 550, and 575 are substantially similar to suture tunnel 42, grooved chamber 48, and elongated body 60 of cannula system 300 of FIG. 2A. As shown in FIG. 2F, in some implementations, cannula system 525, which includes an example elongated body 64 measuring approximately 95 mm, includes a locking component 44 which can be adjusted across a 15 mm range along and within grooved chamber 70 to secure suture 24. In some implementations, cannula system 550, which includes an example elongated body 66 measuring approximately 120 mm, includes a locking component 44 which can be adjusted across a 20 mm range along and within grooved chamber 72 to secure suture 24. In some implementations, cannula system 575, which includes an example elongated body 68 measuring approximately 130 mm, includes a locking component 44 which can be adjusted across a 20 mm range along and within grooved chamber 74 to secure suture 24. Additionally, in some implementations, suture tunnels 76, 78, and 80, which can be substantially similar to suture tunnels 42 of FIG. 2A, measure approximately 70 mm, 90 mm, and 110 mm in cannula systems 525, 550, and 575, respectively.

Figure 2G:
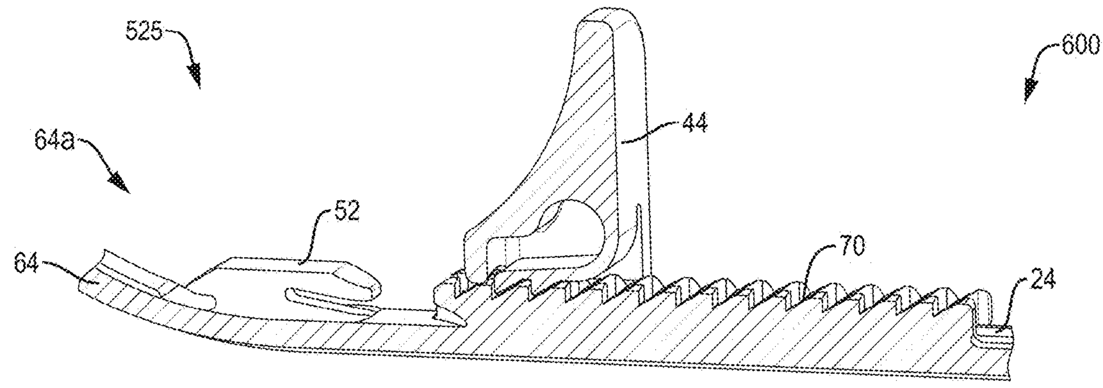
FIG. 2G illustrates an example of the dynamic between the locking component and grooved chamber of the cannula systems of FIGS. 2A and 2F, in a zoomed-in perspective view.

FIG. 2G illustrates example view 600 of the cannula systems of FIGS. 2A and 2F, with particular focus on the dynamic between locking component 44 and the respective grooved chamber surrounding suture 24. View 600 will be referenced to include the components of cannula system 525, however, each component is referred to interchangeably with its substantially similar counterparts in cannula systems 300, 550, and 575. In some examples, such as in FIGS. 2A, 2F, and 2G, locking component 44 is an internal component within cannula systems 525, 550, and 575, rather than an external locking component which can be separately introduced as needed, as in FIG. 2D. However, external locking components are also possible as alternate examples. The present example of cannula systems 525, 550, and 575 also includes one or more suture tunnels 46, which can include suture tunnels 42, which may operate similarly to suture tunnels 42 of cannula systems 200 and 300 to provide additional security to suture 24 during usage by permitting the introduction of an additional external locking component, as shown in FIG. 2D. However, as shown in FIG. 2F, one or more suture tunnels 46 also can include grooved chamber 48 to facilitate the sliding and securing functionality of locking component 44 within cannula systems 525, 550, and 575 at proximal ends 64a, 66a, and 68a of elongated bodies 64, 66, and 68, respectively. In this way, suture 24 can be readily adjusted and re-secured for tautness and/or slack with additional adjustability, even as suture 24 may be tied, fastened, or otherwise secured to proximal securing component 52 for a baseline level of suture security, similar to the dynamic provided by proximal securing component 32 of cannula systems 200 and 300 in previous Figures.

Figure 2H:
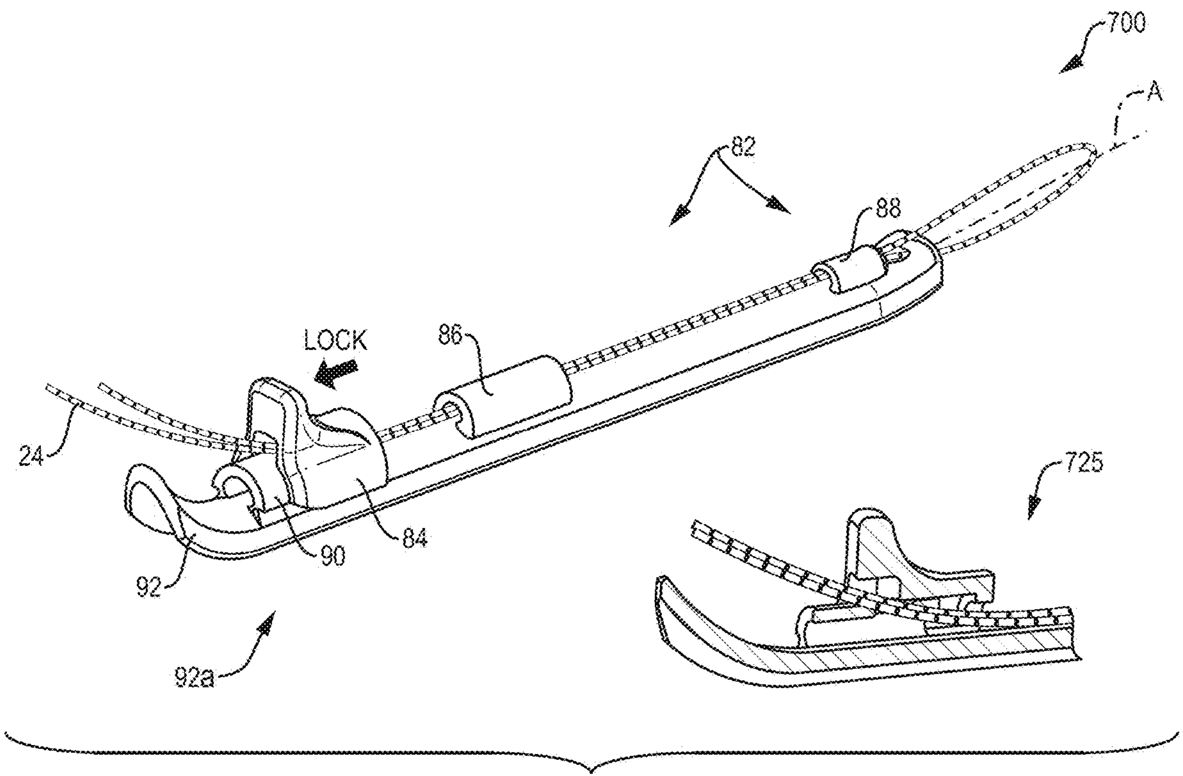
FIG. 2H illustrates an example of a fifth cannula system providing a single tunnel when engaged with an internal locking component, in a perspective view.

FIG. 2H illustrates an example of cannula system 700 when engaged with an internal locking component 84. As with cannula systems 100, 200, 300, 525, 550, and 575, alternate implementations of the proposed approach may vary in the way the suture cooperates with the cannula within a cannula system. However, there may also be some structural differences. For example, locking component 84 of cannula system 700, as shown in view 725, is slidably configured to further secure and/or lock suture 24 into a preferred length and/or tautness during use of cannula system 700. As mentioned, in some examples, locking component 84 is an internal component within cannula system 700, rather than an external locking component which can be separately introduced as needed, as in FIG. 2D. However, alternate internal flexible features and/or external locking components are also possible as alternate examples to provide locking/unlocking of suture 24. The present example of cannula systems 700 also includes one or more suture tunnels 82, which can include suture tunnels 86 and 88, can enclose and stabilize suture 24 within cannula system 700, much like one or more suture tunnels 20 of cannula system 100 or suture tunnels 40 within cannula system 200. Similarly to as shown in cannula system 400 in FIGS. 2D and 2E, and unlike in cannula systems 100, 200, 300, and 525-575, no additional securing mechanism is present in cannula system 700, by which suture 24 may be secured. Instead, as shown in view 725, suture 24 can extend within and through a nexus of locking component 84 and proximal securing component 90 at proximal end 92a of elongated body 92 to permit engagement of suture 24 to be locked/unlocked. In this way, locking component 84 can be engaged to lock/unlock around suture 24 to provide tension adjustment for tautness and/or slack as the means of primary/sole length adjustability. Unlocking suture 24 can also allow for disassembly of cannula system 700. This can allow for more dynamic adjustability of suture 24 length during usage by not requiring initial tying, knotting, or other baseline securing to the cannula system.

Figure 3:
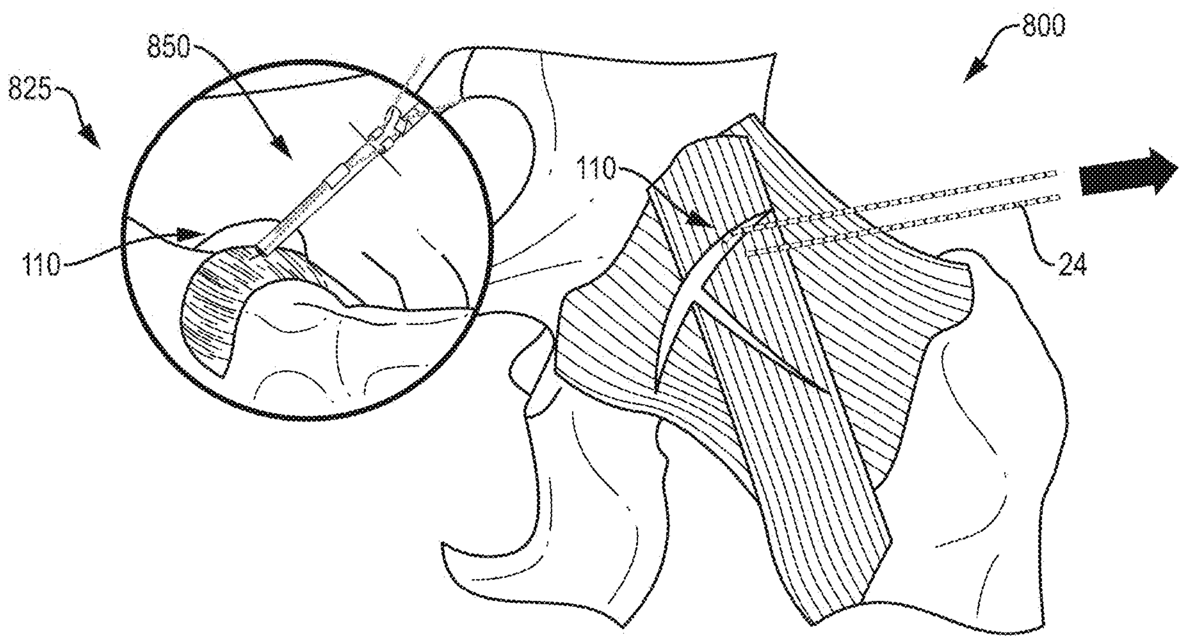
FIG. 3 illustrates an example of the cannula systems of the present disclosure when engaged in patient treatment, in perspective and zoomed-in perspective views.

FIG. 3 illustrates an example 800 of the cannula systems of the present disclosure when engaged in patient treatment, including zoomed-in perspective view 825. In some implementations, once the initial procedure, such as a capsulotomy (incision through the hip capsule) is completed, a traction suture, such as suture 24, can be placed through the capsule tissue at surgical site location 110, which can be retracted to improve visualization. The suture 24 can then be threaded through the portal/passageway/channel of the cannula system 850, which can include any of those previously discussed, to control/manage the suture 24 and keep the suture 24 from interfering with instruments, implants and/or other sutures which may be used in the procedure. Once the suture 24 is loaded into the cannula system 850, there are multiple means to secure the tension of suture 24. For example, the suture 24 can be tied, cleated, or wedged to secure the desired tension. Additionally, in some implementations, suture 24 can be further secured by a locking component/foot, such as locking component 54.

Figure 4A:
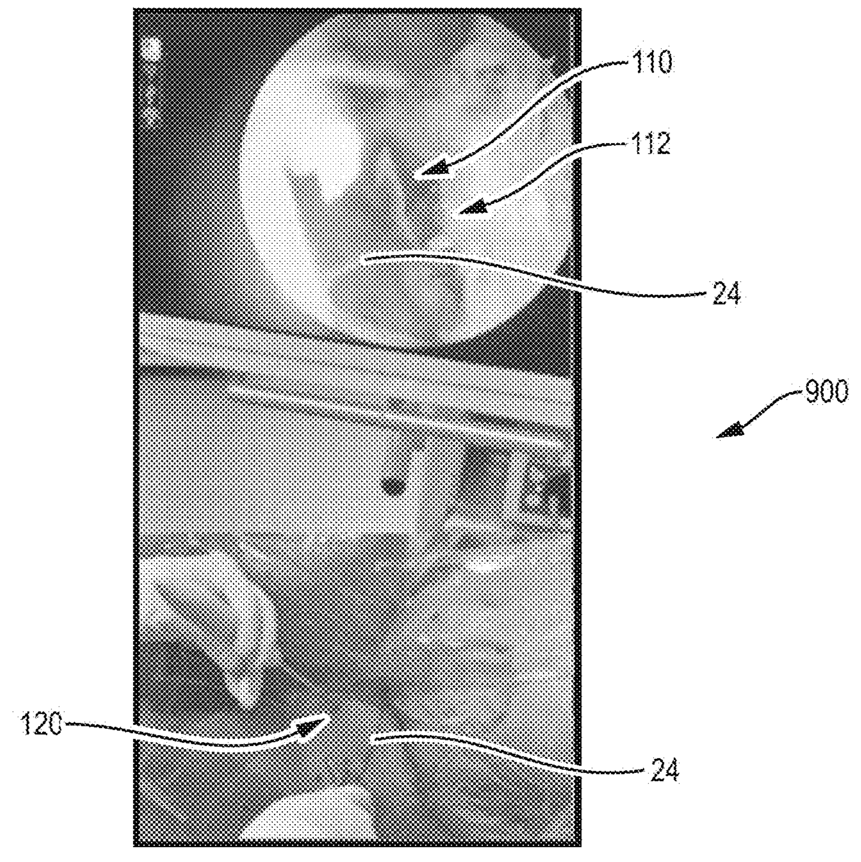
FIGS. 4A-4E provide example photographs illustrating an example process for utilizing the cannula systems of the present disclosure during patient treatment.
Figure 4B:
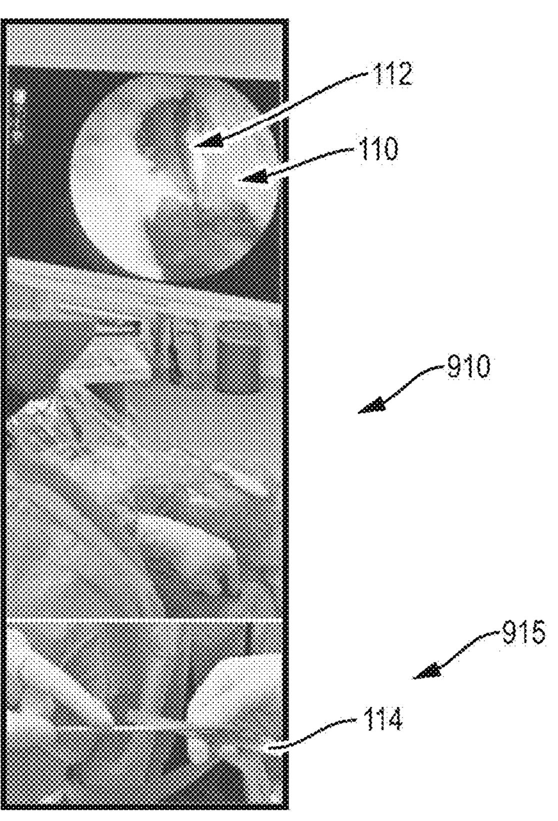
Figure 4C:
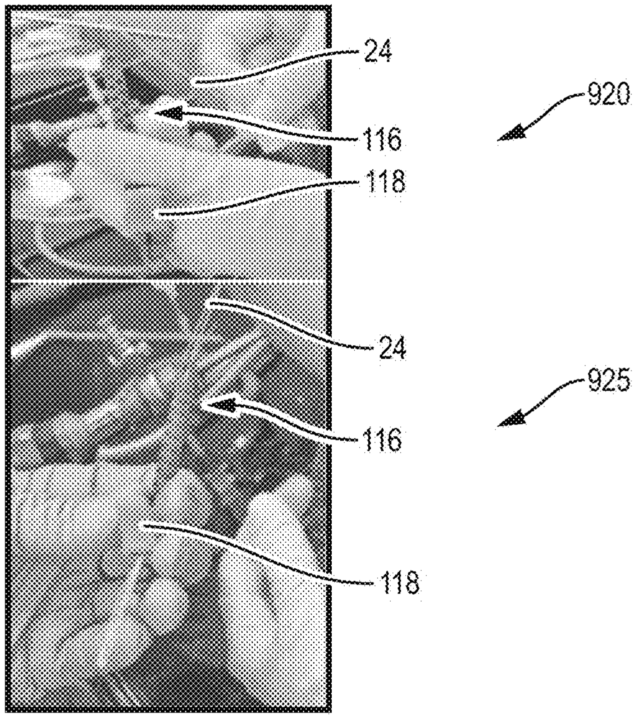
Figure 4D:
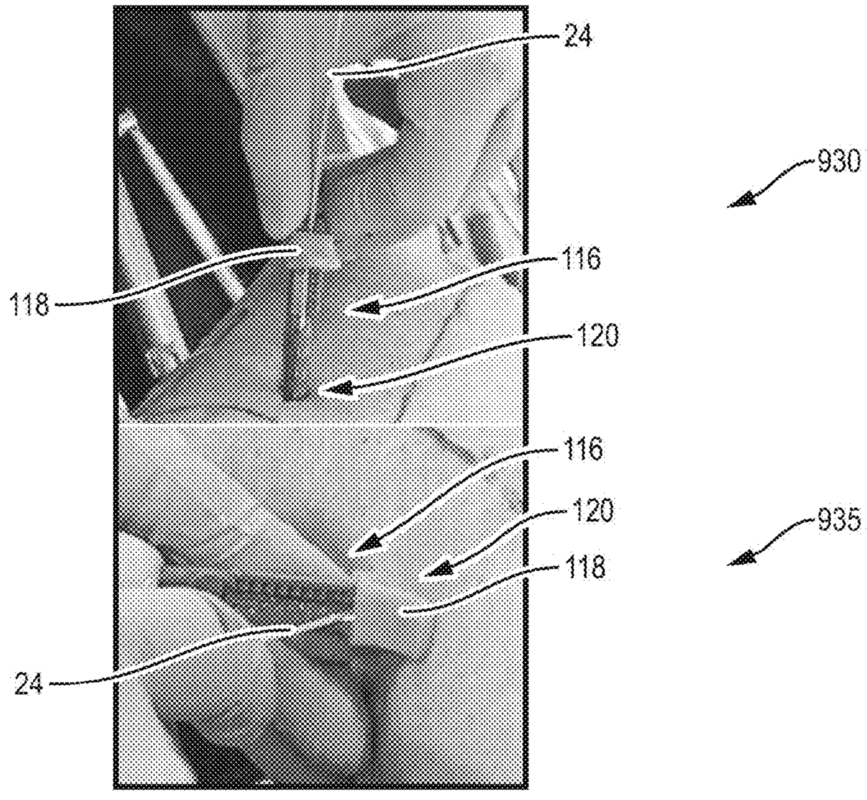
Figure 4E:
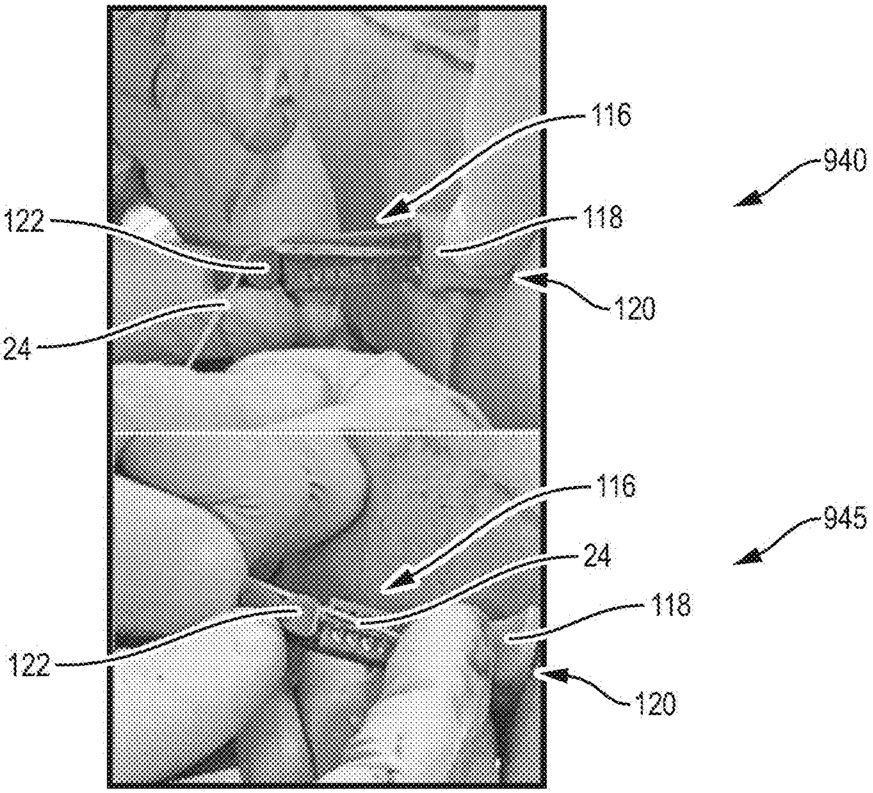

FIGS. 4A-4E provide example photograph views 900-940 illustrating an example process for utilizing the cannula systems of the present disclosure during patient treatment. This example process is similar to that introduced in FIG. 3. In FIG. 4A, view 900 details a user/surgeon passing traction suture 24 through skin site 120 to reach hip capsule 110 during a surgical procedure at surgical treatment site 112. In FIG. 4B, views 910 and 915 show the surgeon measuring the portal depth from skin to the capsule 110 with instrument 114, as discussed in FIGS. 2E and 2F. In FIG. 4C, views 920 and 925 detail threading suture 24 through a cannula body to form a cannula system 116, which can include but are not limited to those introduced previously in the disclosure. Suture 24 may thereby be held taught to provide a straight path for the cannula system 116 at its distal end into the joint via the surgeon's preferred pathway. FIG. 4C also shows locking component 118, which may be similar to those introduced in FIGS. 2A, 2G, and 2F, along with others. In FIG. 4D, views 930 and 935 detail inserting the cannula system 116 into the surgical treatment site 112 (not shown), and in some implementations, subsequently adjusting locking component 118 to secure it against the patient's skin at site 120. As previously discussed, this can help retain the tension of suture 24 throughout the surgical procedure, while still allowing for the temporary increase in tension by pulling the traction suture ends at 122 of cannula system 116 for certain surgical tasks, if necessary. In FIG. 4E, views 940 and 945 illustrate how once cannula system 116 is sufficiently inserted within site 120 toward surgical site 112 and locking component 118 is secured against site 120, suture 24 can be secured against a proximal securing component 122 of cannula system 116, which may be similar to those introduced. Once the desired tension of suture 24 is achieved around proximal securing component 122, suture 24 can be cleated, wedged, tied, and/or otherwise secured by the surgeon.

FIGS. 5A-5E illustrate an example of cannula system 1000. As with cannula systems 100, 200, 300, 525, 550, 575, and 700, alternate implementations of the proposed approach may vary in the way the suture cooperates with the cannula within a cannula system and may utilize processes disclosed in FIGS. 3-4E and 6A-B. However, there may also be some structural differences. For example, in FIG. 5A, the proximal end 102 of the body may comprise a textured gripping surface. Furthermore, in FIG. 5E, similarly to cannula system 100, suture 24 can be threaded through the one or more suture tunnels 98 of cannula system 1000 to control/manage the suture 24 and keep the suture 24 from interfering with instruments, implants and/or other sutures that may be used in a surgical procedure along first surface 16. Second surface 18 is configured to be engaged by hemostats 136 when cannula system 1000 is compressed against the skin of a patient during a surgical procedure. In some implementations, this creates elevation of a tissue, such as a hip capsule. In system 1000, the length of second surface 18 will be about 35 mm between proximal securing component wings 94a and 94b and one or more suture tunnels 98. However, there as there are multiple length cannulas, the length of this may vary with the specific cannula system used. The hemostat may be further configured to maintain contact with the patient at an insertion site to further secure the limbs of the suture 24 during use of the cannula 1000.

Figure 5A:
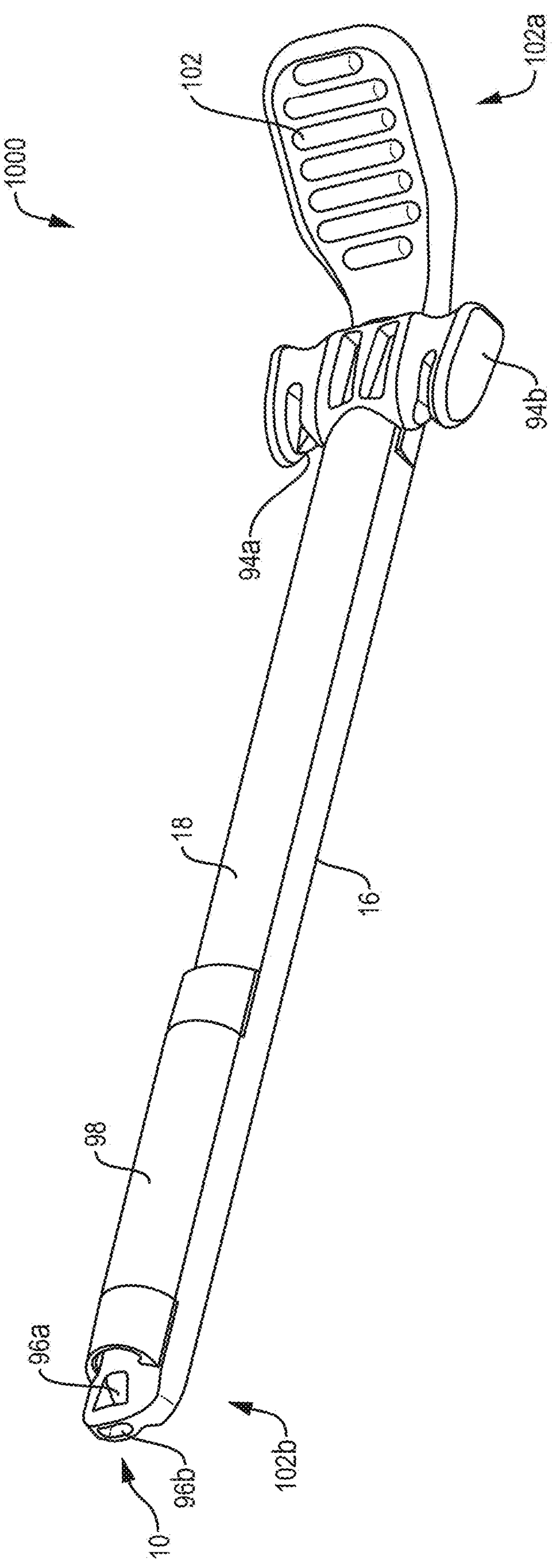
FIGS. 5A-5E illustrate an example of an additional cannula system winged proximal securing components, in perspective (FIGS. 5A, 5E), zoomed-in (FIG. 5B), side (FIG. 5C) and bottom (FIG. 5D) views.
Figure 5B:
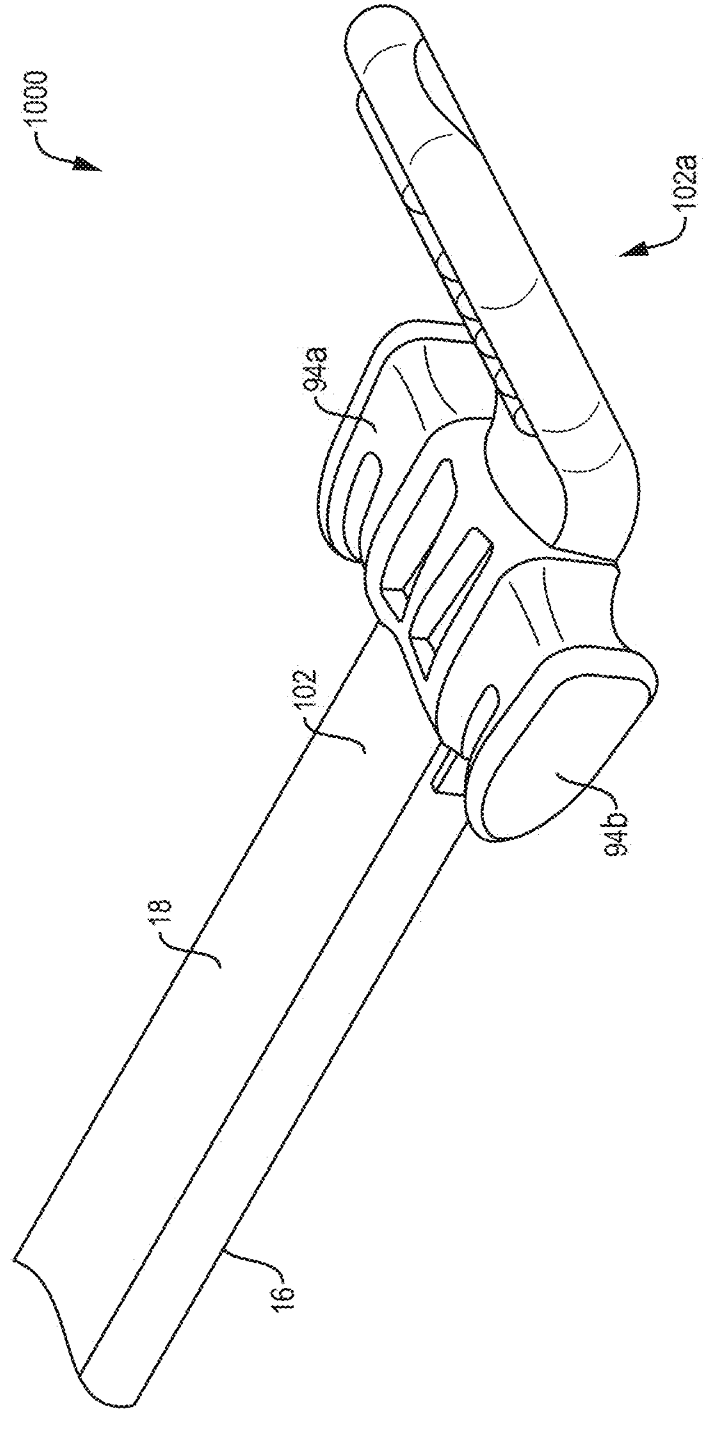
Figures 5C, 5D:
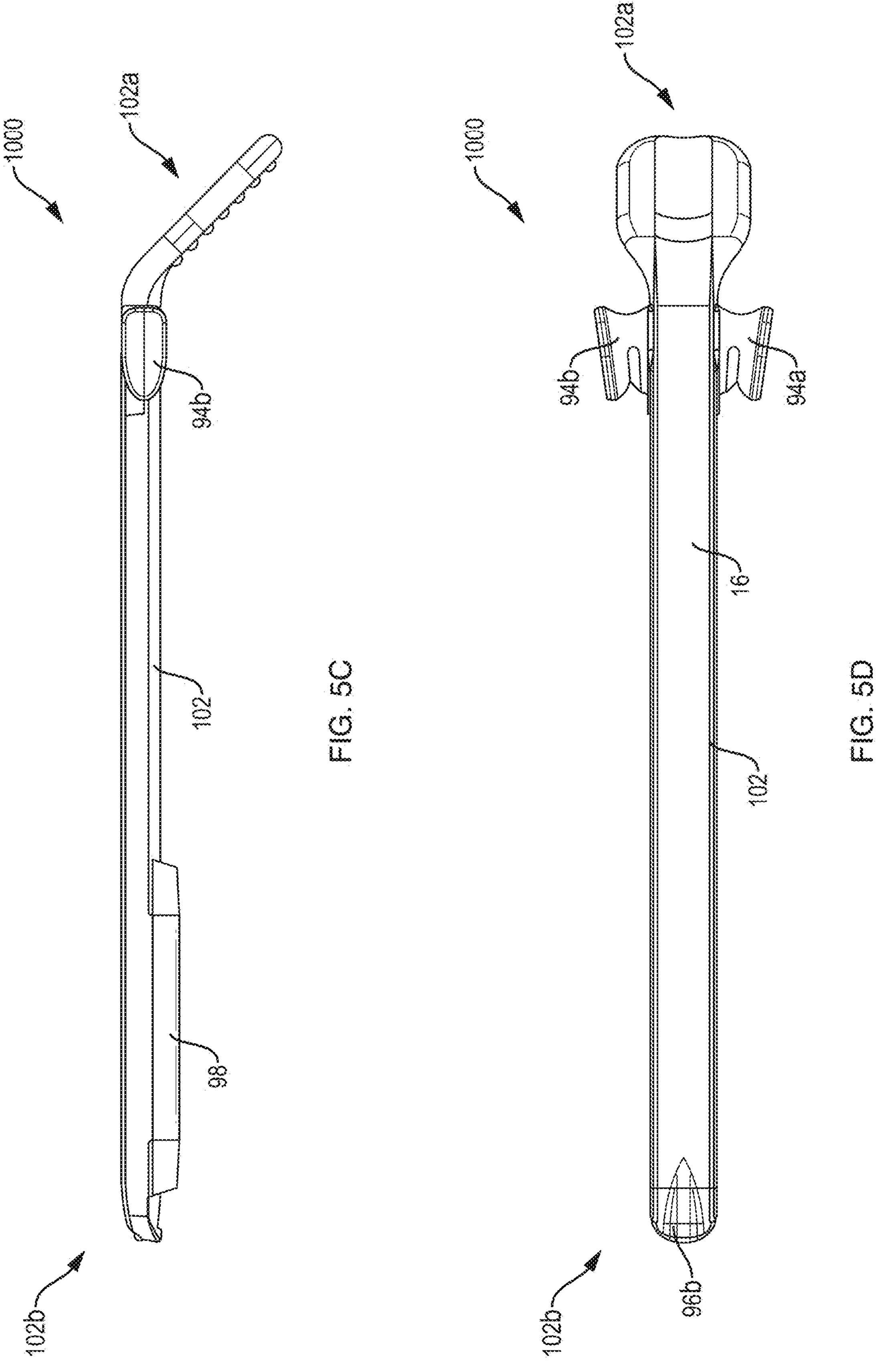
Figure 5E:
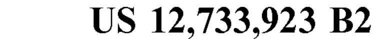
Figure 5E:
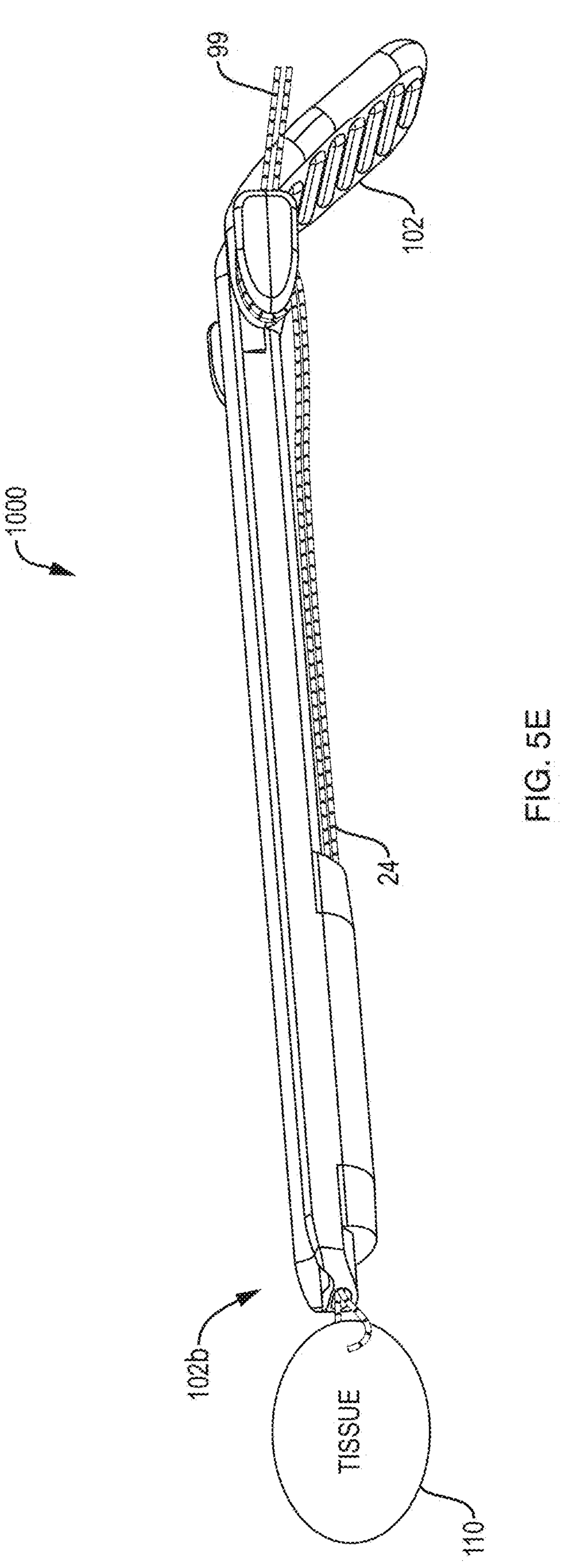

As illustrated in FIGS. 5A-5E, suture 24 can be tied, fastened, or otherwise secured to one or more proximal securing components, including wings 94a and 94b, at proximal end 102a of elongated body 102. This orientation of cannula system 1000 can allow the surgeon to pull/adjust the suture 24 during usage without unsecuring, untying, and/or uncleating the suture 24. In some implementations, this will increase displacement of the hip capsule temporarily to gain better temporary visualization for a certain task within the surgery. For example, the cannula system 1000 can allow the surgeon to use the secured suture 24 via proximal securing component wings 94 and 94*b* to create traction on the hip capsule 110 to improve visualization. As a result, the surgeon may not have to create additional incisions to add traction. The cannula system's 1000 first and second openings 96*a* and 96*b* can thereby manage the traction suture 24 and keep it from interfering with, for example, instruments and implants that may pass through eyelet 10 and one or more suture tunnels 98 to the surgical site at distal end 102*b*. In some implementations, the use of quick suture locking features (i.e. cleats) can allow the surgeon to quickly lock, unlock, adjust the tension of suture 24 as needed throughout the procedure. In some implementations, suture 24 cleats may start with a 0.006" opening, and taper down to a point. This design intent allows for a surgeon to pull one or multiple Ø0.020" suture 24 into the cleat, and have the suture 24 compress within the cleat, such that it locks within a slit of the one or more proximal securing components 94*a* and 94*b*. This feature should allow suture 24 to be easily pulled in, and then compressed to an amount that achieves the desired suture 24 cleat force requirement within each cannula system. One or more monofilaments 99 of the suture 24 can extend from proximal securing components 94*a* and 94*b*, as shown in FIG. 5D. These monofilament tail(s) 99 can additionally be pulled and/or engaged to lead traction onto suture 24 of the cannula system 1000 itself during usage.

For example, for each of the aforementioned canula systems, a suture, such as suture 24, may be routed through a cannula system via a monofilament. The monofilament may be pre-loaded through holes that the capsule suture 24 eventually may pass through. When the capsule suture 24 is passed through tissue, such as the hip capsule, the two tails of the capsule suture 24 are put into a loop(s) of the monofilament(s). The tails of the monofilament(s) may then be pulled to shuttle the capsule suture 24 through the cannula system. The capsule suture 24 may then preferably be held tight, and then the cannula may be 'ziplined' (by rotating back and forth, as would occur on a zipline) down into the joint space. At this point, positioning of the cannula may be confirmed at the tissue site 110, and the suture 24 may be fixed (cleated) to the proximal end of the cannula.

Figure 6B:
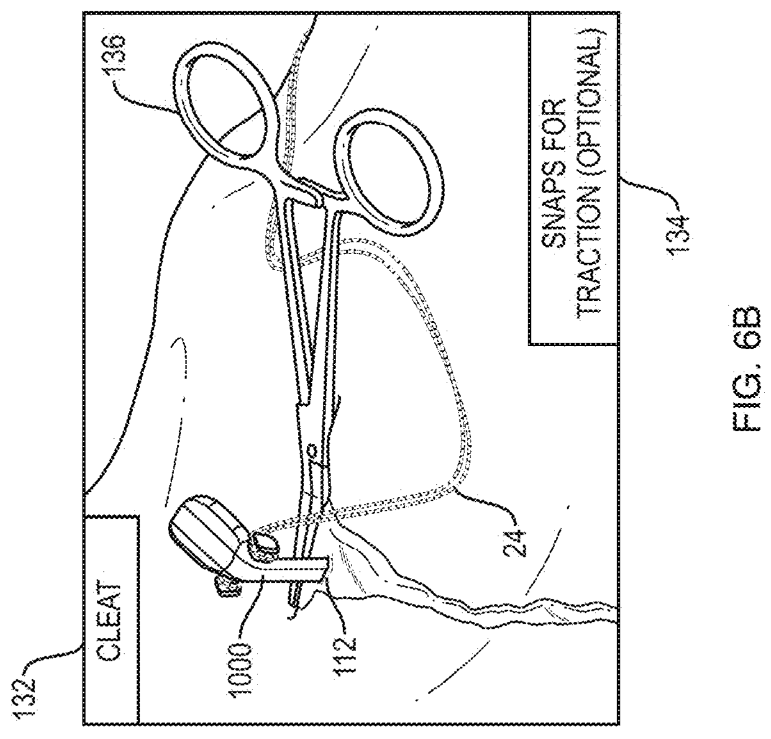
FIGS. 6A and 6B illustrate an example of the cannula systems of the present disclosure when engaged in patient treatment, in perspective and zoomed-in perspective views.
Figure 6A:
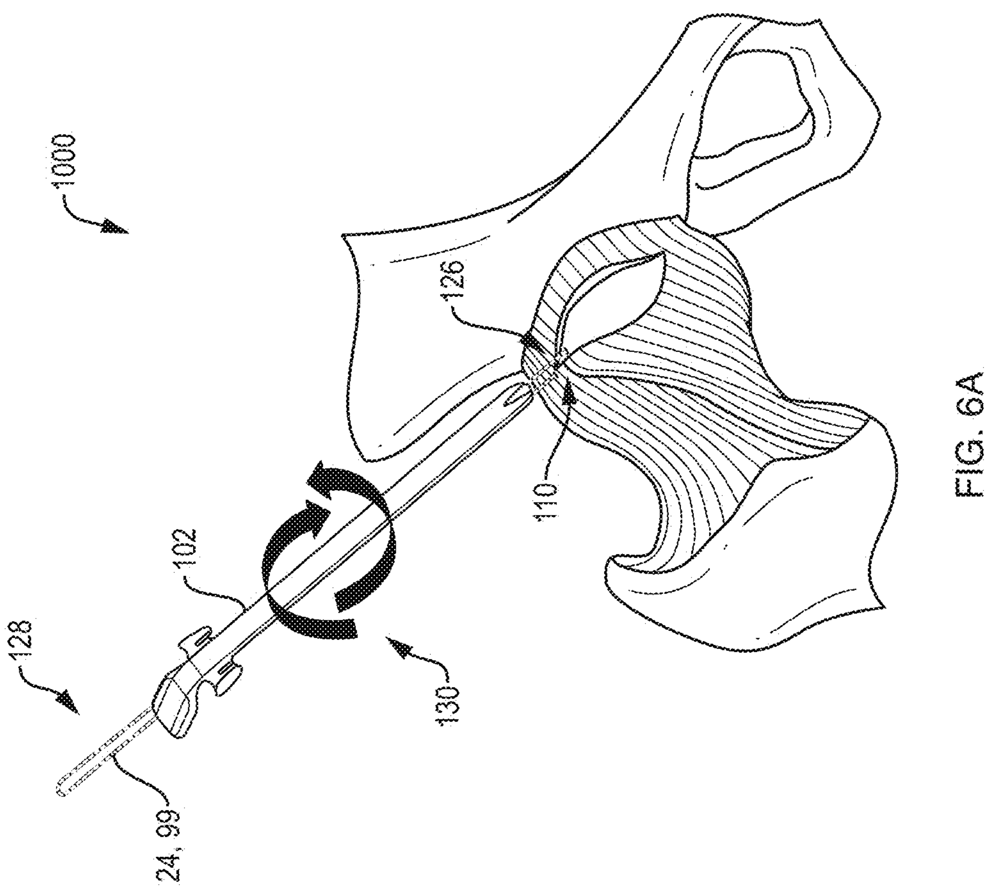

FIGS. 6A and 6B illustrate an example process 1100 for utilizing the cannula systems of the present disclosure during patient treatment. This example process 1100 is similar to that introduced in FIGS. 3 and 4A-4E. For this exemplary process 1100, cannula system 1000 is referenced. In Step 126, a surgeon may generally pass one or more traction sutures 24 through the hip capsule 110 to pull it back to improve the view of the surgical site 112. At Step 128, the desired suture 24 tension of the cannula system 1000 may be set by the surgeon. Step 130 provides that a surgeon or other operator of cannula system 1000 may manipulate elongated body 102 to institute a "zipline with twisting motion" to properly secure cannula system 1000 against the surgical site 112. Suture 24 may then be cleated via proximal securing component wings 94*a* and 94*b* at Step 132 to provide desired tension, while also allowing for monofilament tail(s) 99 to additionally be pulled and/or engaged to lead traction onto suture 24 of the cannula system 1000 to increase tension while remaining cleated. At Step 134, suture 24 tension may be held with hemostats 136 at the skin level, or opened and inserted into skin to lock against skin and preserve tension of suture 24 and/or the cannula system 1000. For example, hemostat 136 jaws may be introduced to clamp over suture 24 and be behind the cannula 1000, but up against the skin 138 to create internal elevation of capsule 110, as the hemostat compresses skin 138 of patient to do so.

Figures 7A, 7B, 7C:
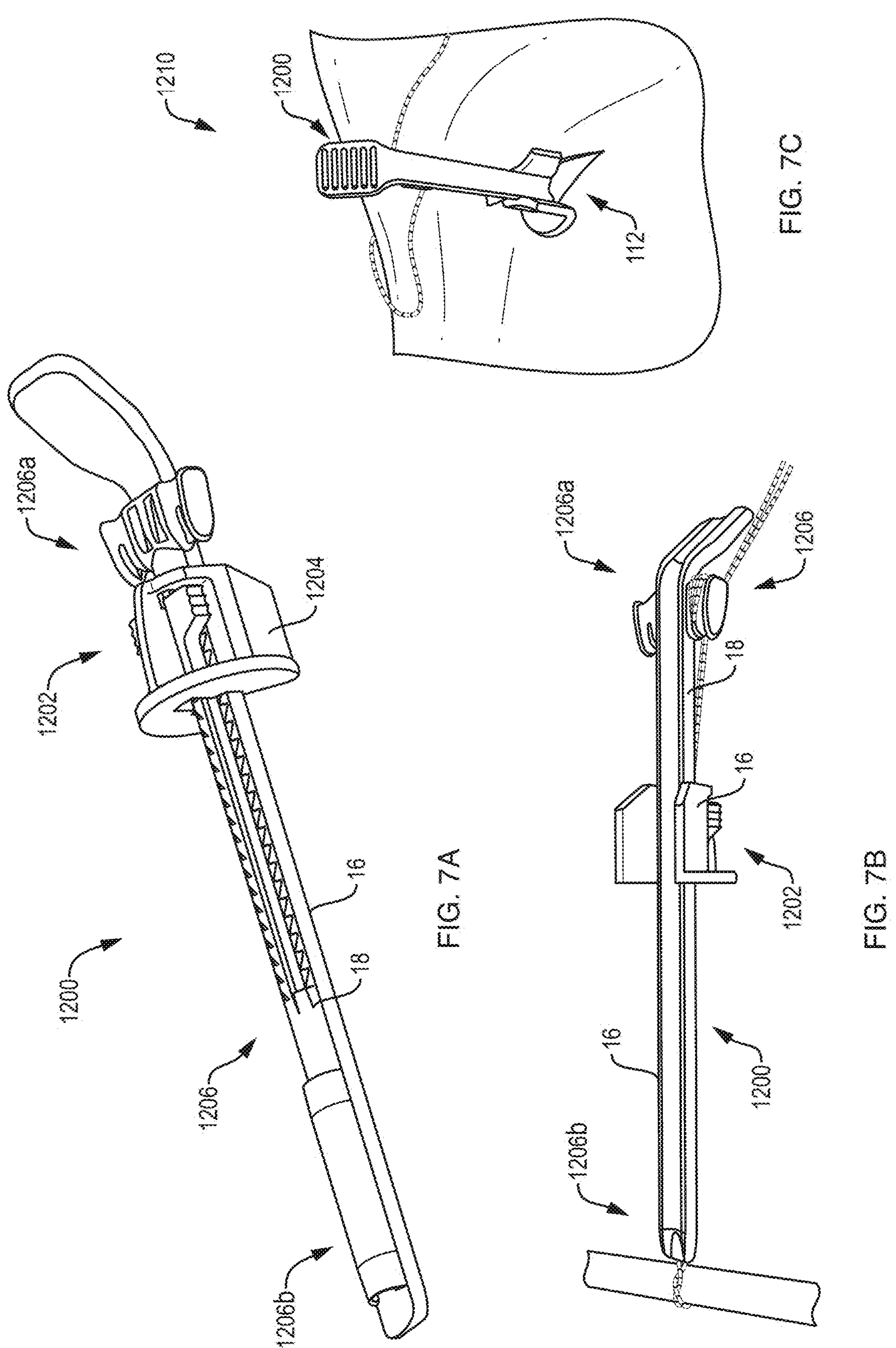
FIGS. 7A and 7B illustrate an example of an additional cannula system with a locking component in perspective views.
FIG. 7C illustrates an example of the cannula systems of the present disclosure when engaged in patient treatment, in a perspective view.

FIGS. 7A-7C illustrate exemplary cannula system 1200. Cannula system 1200 is much like cannula system 1000, and can function according to the processes previously described, including method 1100. However, cannula system 1200 further includes locking component 1202. Locking component 1202 functions similarly to previously described locking components. In FIG. 7A, the foot 1204 of component 1202 is introduced to cannula system 1200. This foot is engaged with first and second surfaces 18 and 16, and can be adjusted in FIG. 7B to descend from proximal 1206*a* to distal end 1206*b* of the elongated body 1206 in order to elevate tissue 110 at site 112 by compressing patient skin, much like hemostat 136 and other disclosed locking components. In system 1200, second surface 18 may include teeth, alike to the teeth of systems 300 and 600, to facilitate the movement of locking component 1202. FIG. 7C provides view 1210 of this exemplary system 1200 during usage.

While the disclosure particularly shows and describes preferred examples, those skilled in the art will understand that various changes in form and details may exist without departing from the spirit and scope of the present application as defined by the appended claims. The scope of this present application intends to cover such variations. As such, the foregoing description of examples of the present application does not intend to limit the full scope conveyed by the appended claims.

The invention claimed is:

1. A cannula comprising:

an elongated body having a proximal end, a distal end, and a longitudinal axis extending therebetween, a first surface configured for passage of a surgical instrument along the first surface, and a second surface opposite the first surface;

a passageway extending along the second surface, the passageway configured for passage of a suture;

an eyelet at least partially defined through the second surface at the distal end of the body for receiving the suture at the distal end; and a proximal securing component defined at the proximal end of the elongated body, wherein the proximal securing component is configured to secure limbs of the suture to the elongated body via a locking component, and wherein the locking component is slidably configured along the second surface to further secure the suture.

2. The cannula of claim 1, wherein the proximal securing component includes one or more securing members against the second surface for securing limbs of the suture passed through the passageway and received at the distal end.

3. The cannula of claim 2, wherein the proximal securing component is configured to secure the limbs of the suture to the elongated body via a knot and/or a cleat.

4. The cannula of claim 3, wherein the one or more securing members include two or more wings configured to secure the limbs of the suture to the elongated body via the knot and/or the cleat.

5. The cannula of claim 3, further comprising one or more suture tunnels disposed along the second surface, the one or more suture tunnels configured for passage of limbs of the suture therethrough.

6. The cannula of claim 5, wherein the second surface is configured to be engaged by one or more hemostats at an insertion site.

7. The cannula of claim 6, wherein the one or more hemostats compress the suture and the second surface at an insertion site to create elevation of a tissue, wherein the one or more hemostats are further configured to maintain contact with a patient at an insertion site to further secure the limbs of the suture during use of the cannula.

8. The cannula of claim 7, wherein a location of the suture at the eyelet is selected to prevent interference with the surgical instrument and/or a surgical implant.

9. The cannula of claim 8, wherein the location of the suture at the eyelet is more distal to facilitate insertion of the cannula through the insertion site to the tissue.

10. The cannula of claim 5, wherein the one or more suture tunnels includes a grooved chamber.

11. The cannula of claim 2, wherein the locking component is configured to allow the suture to be adjusted during usage without unsecuring the suture from the securing member.

12. The cannula of claim 2, wherein the proximal end of the elongated body comprises a textured gripping surface.

13. The cannula of claim 1, wherein the locking component includes a foot.

14. A method for implanting a surgical device, comprising:

securing a suture to a tissue in a joint space;

threading the suture through a cannula to form a cannula system, the cannula system comprising:

an elongated body having a proximal end, a distal end, and a longitudinal axis extending therebetween, a first surface configured for passage of a surgical instrument along the first surface, and a second surface opposite the first surface;

a passageway extending along the second surface, the passageway configured for passage of the suture;

an eyelet at least partially defined through the second surface at the distal end of the body for passage of the suture through the distal end of the elongated body; and one or more securing members against the second surface for securing limbs of the suture passed through the passageway and passed around the distal end a proximal securing component defined at the proximal end of the elongated body, wherein the proximal securing component is configured to secure limbs of the suture to the elongated body via a locking component, and wherein the locking component is slidably configured along the second surface to further secure the suture; and moving the cannula along the suture such that the distal end of the elongated body enters the joint space.

15. The method of claim 14, further comprising:

inserting the cannula system through the external surgical site;

cleating the suture to the elongated body; and adjusting the suture against the patient.

16. The method of claim 15, wherein the second surface is configured to receive one or more hemostats, wherein the one or more hemostats compress the suture and the second surface at an insertion site to create elevation of the tissue, wherein the one or more hemostats are further configured to maintain contact with a patient at an insertion site to further secure the limbs of the suture during use of the cannula.

17. The method of claim 15, wherein the locking component is configured to allow the suture to be adjusted during usage without unsecuring the suture from the securing member.

* * * * *